United States Patent [19]

Collins

[11] 4,068,531

[45] Jan. 17, 1978

[54] MOLTEN METAL SAMPLER

[76] Inventor: William J. Collins, 7005 Madison St., Merrillville, Ind. 46410

[21] Appl. No.: 690,054

[22] Filed: May 26, 1976

Related U.S. Application Data

[62] Division of Ser. No. 595,155, July 11, 1975, Pat. No. 4,002,073.

[51] Int. Cl.² .............................................. G01N 1/12
[52] U.S. Cl. .............................................. 73/425.4 R
[58] Field of Search ............. 73/425.4, 425.6, DIG. 9

[56] References Cited

U.S. PATENT DOCUMENTS

| | | | |
|---|---|---|---|
| 3,315,529 | 4/1967 | Feichtinger | 73/DIG. 9 |
| 3,415,124 | 12/1968 | Collins | 73/425.4 R |
| 3,501,963 | 3/1970 | Collins | 73/425.4 R |
| 3,552,214 | 1/1971 | Collins | 73/425.4 R |
| 3,656,338 | 4/1972 | Collins | 73/425.4 R |
| 3,913,404 | 10/1975 | Boron | 73/DIG. 9 |

Primary Examiner—S. Clement Swisher

[57] ABSTRACT

The invention involves providing a pair of devices or samplers for obtaining different samples of a hot liquid, such as molten metal.

10 Claims, 3 Drawing Figures

MOLTEN METAL SAMPLER

BACKGROUND

This application is a division of my application Ser. No. 595,155 filed on July 11, 1975, now U.S. Pat. No. 4,002,073.

A multitude of Patents have issued relative to obtaining samples of molten metal and quite a number appear to have utilized certain of the technology disclosed in some of my Patents, such as for example, U.S. Pat. No. 3,415,124 dated Dec. 10, 1968 and U.S. Pat. No. 3,415,125 dated Dec. 10, 1968; at least to the extent of utilizing a pair of half sections which are constructed to provide a primary chamber for receiving a sample and a refractory tube carried by the sections for receiving molten metal for flow into the chamber.

The devices of the subject invention generally embody the above components and include certain additional elements with respect to design and construction as will appear hereinafter.

OBJECTIVES

One of the important objectives of the invention is to provide an elongated device comprising, among other things, an elongated casing, a support therein, wall structures which forms a primary chamber and a tubular extension constituting what may be termed one extremity of the device which is supported by the casing, a pair of telescopically connected refractory tubes which are communicatively connected to the chamber and may be considered to be an opposite extremity of the device which is carried by the support. Otherwise expressed, the opposite extremites of the device are preferably respectively supported by the casing and support at only longitudinally spaced locations within the confines of the casing whereby to assist in mounting the components in their correct operative relation to provide a stable device for use.

A significant objective of the invention is to provide a device of the above character which is preferably mounted in one end of an elongated housing or tube in such a way that after a sample is obtained the device may be readily released from the housing.

A particular object of the invention is to provide a device in which the half sections are provided with heat dissipating means and in which heat dissipating means of a different character is disposed in the casing and about portions of the device whereby to expedite and promote uniform cooling of the sample received.

Also, an object is to provide structure comprising an elongated casing and a pair of dissimilar devices which are secured in the casing in a unique manner.

A specific object is to provide a device which includes an improved form of a shield or protector for the entrance end of the device.

A specific objective is to provide a device of a particular shape or configuration whereby to facilitate entry of the device into a mass of molten metal and which minimizes erruption or splash when the device is introduced into the mass. Otherwise expressed, the device is rectangular cross-section compared to one which is round and offers appreciably less resistance to penetration of the molten metal and a sheath and/or shield substantially prevents erruption or splash, thereby affording protection to an operator.

Additional objects and advantages of the invention will become apparent after the description hereinafter set forth is considered in conjunction with the drawings annexed hereto.

DRAWINGS

DESCRIPTION

Figure 1:
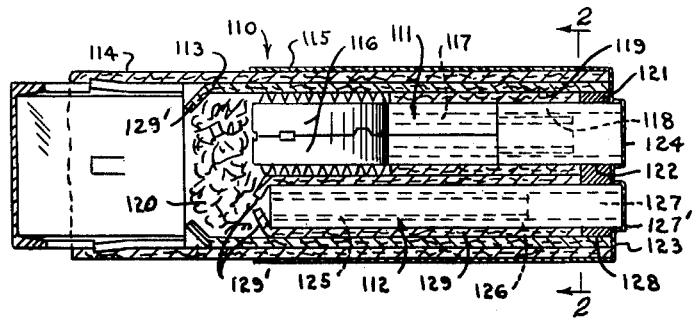
FIG. 1 is a horizontal section of a device or structure having a pair of different receiving means for obtaining different forms of samples.
Figure 2:
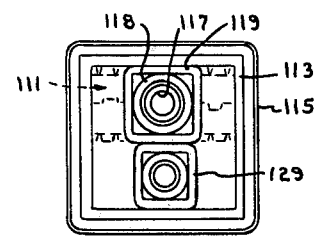
FIG. 2 is a transverse section taken substantially on line 2—2 of FIG. 1.
Figure 3:
FIG. 3 is a perspective view of a sample obtained from one of the receiving means of FIGS. 1 and 2.

The structure is generally designated 110 and is exemplified in FIGS. 1 and 2 whereby different forms of samples may be obtained at substantially the same time. More particularly, the structure 110 comprises, among other things, a device or receiving means generally designated 111 for obtaining a sample, for example, similar to the sample shown in FIG. 13 and a device or receiving means generally designated 112 which serves to obtain a sample, for example, as shown in FIG. 3.

The devices 111 and 112 are preferably secured in a side-by-side relation within the confines of a tubular casing 113, the latter of which is like the casing 40 of the device 3. This casing is surrounded by a housing 114 and the latter by an outer metal jacket or sheath 115 which respectively correspond to those of device 3.

The device 111 comprises a pair of half sections 116, a pair of telescopically connected refractory tubes 117 and 118, and a sleeve 119, substantially square in cross-section and constructed of pasteboard is preferably disposed about the outer tube 118 and tubular formation of the half sections. Fibrous insulating material 120 is disposed in the casing 113. A support or member 121 is provided with a round opening 122 through which the outer tube 118 extends for support and its outer face is preferably located in a flush relation to the outer marginal end edges of the casing, housing, and sheath, and a shield 123 is secured against the aforesaid face and edges and is provided with a pocket or recess 124, which, as shown, receives the outer end of the outer tube 118. The sheath including the shield, as above referred to, penetrate the molten metal through the layer of scum and the shield disintegrates so that some of the molten metal may flow into the tubes 117 and 118 for reception in the primary chamber and secondary chambers formed by the half sections.

The device 112 preferably comprises an inner elongated refractory tube 125 and an outer refractory tube 126 having an inner extremity fitted over the outer end of the inner tube and an outer extremity which projects beyond the inner tube 125 to provide an enlarged cylindrical entrance 127 which initially receives the molten metal. The support 121 is provided with a round opening 128 through which the outer tube extends for support and the shield 123 is provided with an additional pocket or recess 127' for receiving the outer end of the outer tube, the latter of which extends a short distance in advance of the member 121 whereby to facilitate entry of the molten metal into the entrance 127.

The tubes 125 and 126 are secured in a casing 129 which is preferably square in cross-section and made of pasteboard. As shown in FIG. 2 an outer side of casing 129 engages one inner side of the casing 113 and an inner side of the casing 129 engages one side of the sleeve 119 and the heat dissipating means on the inner face of one of the half sections. An opposite side of the sleeve 119 engages an opposite side of the casing 113 and the heat dissipating means on the other half section engages an opposite side of the casing 113. The diametrically opposed peripheral surfaces of the enlarged or head portions of the half sections also engage opposed inner parallel surfaces of the casing 113, all for the purpose of locating and stabilizing the positions of the components. It should be noted that the casing 129 has an inner end provided with internal portions 129' which define a vent and stops for the tubes and that the wool 120 is located in the inner extremity of the casing 113 and is common to the devices 111 and 112 whereby to minimize outflow of metal therefrom. The sleeve 119 and casing 129 assist in holding certain of the components assembled and also serve as buffer means.

SUMMARY

In view of the foregoing it should be manifest that the various devices embody improved principles of design and construction whereby samples of molten metal can be expeditiously obtained. Of particular significance is the fact that the subassemblies or units of the devices are substantially supported only at their extremities but firmly in order to stabilize the units in a casing for use.

Having thus described my invention, it is obvious that various modifications may be made in the same without departing from the spirit of the invention, and therefore, I do not wish to be understood as limiting myself to the exact forms, construction, arrangements, and combinations of parts herein shown and described.

I claim:

1. Structure comprising a casing, a pair of dissimilar devices disposed in said casing in a side-by-side relation for respectively receiving different forms of samples of molten metal, a support secured in said casing and provided with a pair of openings respectively receiving portions of said devices, one of said devices comprising a pair of mating sections defining a chamber, a pair of telescopically connected glass tubes for receiving molten metal for flow into said chamber, with one of said tubes extending through one of said openings, /and/ the other of said devices comprising a pair of telescopically connected glass tubes with one of these tubes extending through the other opening in said support, an elongated tubular housing surrounding said structure, and said casing being provided with means for engagement by a member insertable into said housing for facilitating release of said casing and devices as a unit from said housing.

2. A device comprising a pair of telescopically engaged tubes for receiving a sample of molten material, an open ended tubular sleeve surrounding and holding said tubes assembled, one of said tubes being longer and forming with the other an enlarged entrance serving to initially receive such a material and the other tube having an outlet which serves to vent said tubes whereby to promote the flow of the material therein.

3. Structure comprising a casing, a pair of dissimilar devices disposed in said casing in a side-by-side relation for respectively receiving different forms of samples of molten material, a support disposed in and supported by said casing and provided with a pair of preformed openings, one of said devices comprising a pair of mating sections defining a chamber, tubular means for receiving molten material for flow into said chamber and having an end extending into one of said openings, /and/ the other device comprising tubular structure having an entrance and extending into the other opening in said support for receiving such material, filter means disposed in said casing assisting to prevent the release of the molten material from said devices, and said casing having an inturned portion assisting to hold said filter material in relation to these devices.

4. Structure comprising a casing, a pair of dissimilar devices disposed in said casing in a side-by-side relation for respectively receiving different forms of samples of molten metal, a support secured in said casing and provided with a pair of openings respectively receiving portions of said devices, one of said devices comprising a pair of mating sections defining a chamber, a pair of telescopically connected tubes for receiving molten metal for flow into said chamber, with one of said tubes extending through one of said openings, the other of said devices comprising a pair of telescopically connected tubes with one of these tubes extending through the other opening in said support, and a pair of sleeves of non-circular cross-section which respectively surround portions of said pairs of telescopically connected tubes.

5. Structure comprising a casing, a pair of dissimilar devices disposed in said casing in a side-by-side relation for respectively receiving different forms of samples of molten metal, a support secured in said casing and provided with a pair of openings respectively receiving portions of said devices, one of said devices comprising a pair of mating sections defining a chamber, a pair of telescopically connected tubes for receiving molten metal for flow into said chamber, with one of said tubes extending through one of said openings, the other of said devices comprising a pair of telescopically connected tubes with one of these tubes extending through the other opening in said support, and an elongated housing having an extremity which surrounds said casing and an opposite extremity for connection with a lance.

6. Structure comprising a casing, a pair of dissimilar devices disposed in said casing in a side-by-side relation for respectively receiving different forms of samples of molten metal, a support secured in said casing and provided with a pair of openings respectively receiving portions of said devices, one of said devices comprising a pair of mating sections defining a chamber, a pair of telescopically connected tubes for receiving molten metal for flow into said chamber, with one of said tubes extending through one of said openings, the other of said devices comprising a pair of telescopically connected tubes with one of these tubes extending through the other opening in said support, an elongated housing having one extremity which surrounds said casing and an opposite extremity for connection with a lance, and said casing being provided with abutment means which may be forcibly engaged by a lance whereby to release said casing and components therein as a unit from said housing.

7. Structure comprising a casing, a pair of dissimilar devices disposed in said casing in a side-by-side relation for respectively receiving different forms of samples of molten material, a support secured in said casing and provided with a pair of openings, one of said devices comprising a pair of mating sections defining a chamber, tubular means for receiving molten material for flow into said chamber and having an end extending into one of said openings, the other device comprising tubular structure having an end extending into the other opening in said support for receiving such material, and a pair of sleeves of non-circular cross-sections respectively surrounding said tubular means and said tubular structure.

8. Structure comprising a non-circular casing, a pair of dissimilar devices disposed in said casing in a side-by-side relation for respectively receiving different forms of samples of molten material, a support secured in said casing and provided with a pair of openings, one of said devices comprising a pair of mating sections defining a chamber, tubular means for receiving molten material for flow into said chamber and having an end extending into one of said openings, the other device comprising tubular structure having an end extending into the other opening in said support for receiving such material.

9. Structure comprising a casing, a pair of dissimilar devices disposed in said casing in a side-by-side relation for respectively receiving different forms of samples of molten material, a support secured in said casing and provided with a pair of openings, one of said devices comprising a pair of mating sections defining a chamber, tubular means for receiving molten material for flow into said chamber and having an end extending into one of said openings, the other device comprising tubular structure having an end extending into the other opening in said support for receiving such material; and an elongated open-ended housing of non-circular cross-section surrounding said casing.

10. Structure comprising a casing, a pair of dissimilar devices disposed in said casing in a side-by-side relation for respectively receiving different forms of samples of molten material, a support secured in said casing and provided with a pair of openings, one of said devices comprising a pair of mating sections defining a chamber, tubular means for receiving molten material for flow into said chamber and having an end extending into one of said openings, the other device comprising tubular structure having an end extending into the other opening in said support for receiving such material, and a pair of sleeves respectively surrounding said tubular means and said tubular structure, a housing surrounding said casing, said casing, sleeves and housing being non-circular in cross-section, and said sleeves abutting one another and said casing and the latter abuts said housing.

* * * * *